United States Patent [19]

Cheminal et al.

[11] Patent Number: 5,616,820
[45] Date of Patent: Apr. 1, 1997

[54] PROCESS FOR THE MANUFACTURE OF 1,1,1,2-TETRAFLUORO-2-CHLOROETHANE AND OF PENTAFLUOROETHANE

[75] Inventors: Bernard Cheminal, Brignais; Eric Lacroix, Lyons; André Lantz, Vernaison, all of France

[73] Assignee: Elf Atochem S.A., France

[21] Appl. No.: 496,052

[22] Filed: Jun. 28, 1995

Related U.S. Application Data

[63] Continuation of Ser. No. 188,333, Jan. 26, 1994, abandoned.

[30] Foreign Application Priority Data

Jan. 27, 1993 [FR] France .................. 93 00780

[51] Int. Cl.⁶ .................. C07C 17/08
[52] U.S. Cl. .................. 570/169; 570/166; 570/168
[58] Field of Search .................. 570/168, 169, 570/166

[56] References Cited

U.S. PATENT DOCUMENTS

| | | |
|---|---|---|
| 2,435,551 | 2/1948 | Black . |
| 2,900,423 | 8/1959 | Smith . |
| 3,650,987 | 3/1972 | Vecchio et al. .................. 570/168 |
| 3,661,805 | 5/1972 | Horvath . |
| 3,787,331 | 1/1974 | Groppelli et al. .................. 570/168 |
| 3,793,229 | 2/1974 | Groppelli et al. .................. 570/168 |
| 3,804,778 | 4/1974 | Ramanadin . |
| 4,131,616 | 12/1978 | Stiles . |
| 4,439,534 | 3/1984 | Foulletier . |
| 4,748,285 | 5/1988 | Foulletier . |
| 4,766,260 | 8/1988 | Manzer et al. .................. 570/168 |
| 4,912,270 | 3/1990 | Carlson et al. . |

FOREIGN PATENT DOCUMENTS

| | | |
|---|---|---|
| 0055652 | 7/1982 | European Pat. Off. . |
| 0128510 | 12/1984 | European Pat. Off. . |
| 2276098 | 1/1976 | France . |
| 2407021 | 5/1979 | France . |
| 2178237 | 7/1990 | Japan . |

*Primary Examiner*—Alan Siegel
*Attorney, Agent, or Firm*—Spencer & Frank

[57] ABSTRACT

The invention relates to a process for the manufacture of 1,1,1,2-tetrafluoro-2-chloroethane and of pentafluoroethane.

The process, which consists of the gas phase catalytic fluorination of at least one pentahaloethane of formula $C_2HX_{2-n}F_{3+n}$ in which X denotes a chlorine or bromine atom and n the number 0 or 1 by means of hydrofluoric acid, is characterized in that there is used a mixed catalyst composed of oxides, halides and/or oxyhalides of nickel and chromium deposited on a support consisting of aluminium fluoride or a mixture of aluminium fluoride and alumina.

23 Claims, No Drawings

PROCESS FOR THE MANUFACTURE OF 1,1,1,2-TETRAFLUORO-2-CHLOROETHANE AND OF PENTAFLUOROETHANE

This is a continuation of application Ser. No. 08/188,333, filed on Jan. 26, 1994, now abandoned.

FIELD OF THE INVENTION

The present invention relates to a continuous process for the manufacture of 1,1,1,2-tetrafluoro-2-chloroethane (F124) and of pentafluoroethane (F125) and more particularly relates to the manufacture of these two compounds by gas phase fluorination of 1,1,1-trifluoro-2,2-dichloroethane (F123) by means of hydrofluoric acid in the presence of a catalyst.

BACKGROUND OF THE INVENTION

As the compounds F124 and F125 can be used as substitutes for perchlorofluorocarbons (CFCs) in the field of aerosols (propellants) and in that of refrigeration, there is currently a search for highly efficient processes for their industrial production.

U.S. Pat. No. 4,766,260 describes a process for synthesis of compounds F123 and F124 by hydrofluorination of perhalogenated olefins in the gas phase, the object being to minimize the formation of F125. Example 13 (column 6) describes the fluorination of tetrachloroethylene with a catalyst $CrCl_3/Al_2O_3$; despite a temperature of 350° C., a long contact time (60 seconds) and a high $HF/C_2Cl_4$ molar ratio (6/1), the selectivities towards F124 and F125 are low (33.3% and 7.2% respectively).

The use of a catalyst based on chromium(III) ($CrCl_3$) supported on carbon for the gas phase catalytic fluorination of halogenated olefins forms the subject of the Japanese Patent Application published under No. 48-72105/73 in which Example 4 describes the fluorination of tetrachloroethylene. There again, despite a reaction temperature of 400° C. and a high (5/1) $HF/C_2Cl_4$ molar ratio, the composition of the products formed is limited to F121 ($CHCl_2-CFCl_2$: 6.8%), to F122 ($CHCl_2-CClF_2$: 10.5%) and to F123 (82.7%).

U.S. Pat. No. 3,258,500 describes the use of mass chromium or chromium supported on alumina for gas phase catalytic fluorination reactions. In particular, Example 17 (column 14) describes the fluorination of tetrachloroethylene. At 400° C., with a $HF/C_2Cl_4$ molar ratio of 6.2/1, the selectivity towards F123+F124+F125 is low (47.7%); a reduction in the reaction temperature (300° C.) improves this selectivity (79.7%) but the distribution is then shifted towards the less fluorinated products (F123 and F124).

Patent Application EP 0,349,298 describes the synthesis of the compounds F123 and F124 from pentahaloethanes by gas phase catalytic fluorination over a catalyst composed of a metal chosen from chromium, cobalt, nickel and manganese deposited on alumina. This document puts the emphasis, on the one hand, on the exhaustive activation of the catalyst with hydrofluoric acid (at least 90% of the support in the form of $AlF_3$ after activation) and, on the other hand, the minimized formation of F125 during the reaction. Thus, in Example 6 which describes the fluorination of F122 at 350° C. and with a long contact time (30 seconds), the selectivity towards F125 is only 1.1% and the cumulative selectivity (F123+F124+F125) is only 71.5%. In Example 5 which describes the fluorination of F123 in the gas phase over a $NiCl_2/Al_2O_3$ catalyst at 400° C., with a contact time of 30 seconds and a HF/F123 molar ratio of 4, the selectivity towards F125 is only 7.5%.

A process for producing fluorinated aliphatic hydrocarbons, based on the fluorination in the gas phase by hydrofluoric acid of halogenated aliphatic hydrocarbons containing at least one halogen atom other than fluorine, forms the subject of U.S. Pat. No. 3,755,477 where the catalyst is a mass chromium oxide treated with steam before calcination and activation with hydrofluoric acid. Example 25 uses such a catalyst for the fluorination of F123 at 390° C. with a high (9.5/1) HF/F123 molar ratio; the selectivities towards F125 and F124 are respectively 67 and 21% but a selectivity of 2.5% towards chloropentafluoroethane (F115), which can not be recycled, is also observed.

From the examination of the state of the art, it appears difficult to synthesize the two desired compounds (F124 and F125) with good selectivity and significant productivity by direct fluorination of tetrachloroethylene or of F122. Starting from tetrachloroethylene, and despite high contact times, temperatures and molar ratios, it seems difficult to obtain F124 and more especially F125 with good yields. The synthesis of these two compounds is easier from F122 but, in this case, a problem of selectivity is encountered (significant formation of by-products).

As regards U.S. Pat. No. 3,755,477, it shows that, from F123, the synthesis of F125 requires a high molar ratio (9.5) and a high temperature (390° C.) leading to the not insignificant concomitant formation of undesirable F115.

Patent Application WO 92/16482 relates to the manufacture of F124 and of F125 by gas phase fluorination of pentahaloethanes, especially that of F123, over a catalyst based on zinc and optionally on another metal deposited on a fluorinated alumina. Despite a high contact time (30 seconds), the best degree of conversion of the F123 obtained in the examples is approximately 60% and the maximum selectivity towards F125 is 28%.

Patent Application FR 2,669,022 describes the use of a catalyst based on nickel and chromium supported on $AlF_3$ or fluorinated alumina for the specific fluorination of F133a ($CF_3-CH_2Cl$) to F134a ($CF_3-CH_2F$), this catalyst making it possible to obtain very good selectivities towards F134a.

In view of the advantage of the compounds F124 and F125 as substitutes for CFCs, their industrial manufacture requires a particularly highly efficient process, that is to say one which makes it possible to obtain:
a very high selectivity towards F124+F125
a high productivity of F124 and/or F125
a high flexibility to direct, as desired, the manufacture towards the production, as the major product, of F124 or towards that of F125, while minimizing the formation of by-products.

A process which makes it possible to achieve this object was described in Patent Application FR 2,661,906 which, for the fluorination of F123, recommends a chromium oxide catalyst supported on active charcoal.

DESCRIPTION OF THE INVENTION

It has now been found that this object can also be achieved by using the mixed Ni/Cr catalyst according to Patent Application FR 2,669,022 relating to the fluorination of F133a to F134a. This type of catalyst makes it possible to obtain an overall selectivity towards F124+F125 of approximately 90% or more.

The subject of the invention is thus a continuous process for the preparation of F124 and/or of F125 by gas phase catalytic fluorination of at least one pentahaloethane of formula $C_2HX_{2-n}F_{3+n}$ in which X denotes a chlorine or bromine atom and n the number 0 or 1 by means of hydrofluoric acid, characterized in that there is used a mixed catalyst composed of oxides, halides and/or oxyhalides of nickel and chromium deposited on a support consisting of aluminium fluoride or of a mixture of aluminium fluoride and alumina.

The starting pentahaloethane is preferably F123, alone or mixed with F123a (1,2-dichloro-1,1,2-trifluoroethane). However, for the preferential manufacture of F125, it is also possible to use, as starting material, F124 itself, its isomer F124a (1-chloro-1,1,2,2-tetrafluoroethane), F123b (1,1-dichloro-1,2,2-trifluoroethane) or a mixture of these compounds.

Although it is preferable to start from chlorinated pentahaloethanes $C_2HCl_{2-n}F_{3+n}$, the process according to the invention can be applied to their brominated homologues such as, for example, 1-bromo-1-chloro-2,2,2-trifluoroethane ($CF_3CHBrCl$), 1,1-dibromo-2,2,2-trifluoroethane ($CF_3CHBr_2$), 1-bromo-2-chloro-1,1,2-trifluoroethane ($CF_2BrCHClF$) or 1,1-dibromo-1,2,2-trifluoroethane ($CFBr_2CHF_2$).

The catalyst to be used in accordance with the present invention can be prepared in a way known per se from an activated alumina. The latter can, in a first stage, be converted to aluminium fluoride or a mixture of aluminium fluoride and alumina by fluorination using air (or an inert gas such as nitrogen) and hydrofluoric acid, the degree of conversion of the alumina to aluminium fluoride depending essentially on the temperature at which the fluorination of the alumina is carried out (generally between 200° and 450° C., preferably between 250° and 400° C.). The support is then impregnated using aqueous solutions of chromium and nickel salts or using aqueous solutions of chromic acid, of nickel salt and of a chromium-reducing agent such as methanol.

When chromic acid ($CrO_3$) is used as chromium precursor, this chromium can be reduced by any means known to one skilled in the art (chemical reducing agent, thermal reduction and the like), with the proviso that the technique used must not harm the properties of the catalyst and thus its activity. The preferred chemical reducing agent is methanol.

As chromium and nickel salts, it is preferable to use the chlorides, but it is also possible to use other salts such as, for example, the oxalates, formates, acetates, nitrates and sulphates or nickel dichromate provided that these salts are soluble in the amount of water capable of being absorbed by the support.

The catalyst used in the process according to the invention can also be prepared by direct impregnation of the alumina by solutions of the abovementioned chromium and nickel compounds. In this case, the conversion of at least part (70% or more) of the alumina to aluminium fluoride is carried out during the stage of activation of the catalyst.

The activated aluminas to be used for the preparation of the catalyst according to the present invention are well-known products which are commercially available. They are generally prepared by calcination of alumina hydrates at a temperature between 300° and 800° C. The activated aluminas which can be used in the context of the present invention can contain significant levels (up to 1000 ppm) of sodium without this harming the catalytic activity.

The catalyst according to the invention can contain, by mass, from 0.5 to 20% of chromium and from 0.5 to 20% of nickel and, preferably, between 2 and 10% of each of the metals in a nickel/chromium atomic ratio between 0.5 and 5, preferably in the region of 1.

Before being able to catalyze the fluorination reaction of the pentahaloethane $C_2HX_{2-n}F_{3+n}$, the catalyst according to the invention must be conditioned, that is to say converted to active and stable constituents (under the reaction conditions) by a prior operation known as activation.

This treatment can be carried out "in situ" (in the fluorination reactor) or else in suitable equipment designed to withstand the activation conditions. Activation generally comprises the following stages:

drying at low temperature (100° to 150° C., preferably 110° to 130° C.) in the presence of air or nitrogen, drying at high temperature (250° to 450° C., preferably 300° to 350° C.) under nitrogen or under air, fluorination at low temperature (180° to 300° C., preferably at approximately 200° C.) by means of a mixture of hydrofluoric acid and nitrogen, the HF content being controlled so that the temperature does not exceed 300° C., and finishing under a stream of pure hydrofluoric acid or hydrofluoric acid diluted with nitrogen at a temperature which can range up to 450° C.

During this operation, the catalytic precursors (nickel and chromium halides, chromate, nickel dichromate, chromium oxide) are converted to corresponding fluorides and/or oxyfluorides, which leads to water and/or hydrochloric acid being given off.

This activation also contributes to increasing the fluorination of the alumina when the impregnation is carried out on a support which is already partially fluorinated or, when the alumina is impregnated directly, to fluorinating the latter. In the latter case, it is necessary to perfectly control the temperature (the fluorination of the alumina is very exothermic) if it is desired not to harm the physical characteristics of the catalyst; moreover, the amounts of water generated are significantly larger.

Chemical analysis of the elements (chromium, nickel, fluorine, aluminium, oxygen), after activation, makes it possible to verify the inorganic composition of the catalyst according to the invention.

In accordance with the process according to the invention, the fluorination reaction of the pentahaloethane by HF can be carried out at a temperature ranging from 250° to 470° C., and more particularly at a temperature between 280° and 410° C. However, if it is desired to direct the reaction towards the preferential synthesis of F124, the reaction will instead be carried out at a temperature in the lower part (300°–330° C.) of the abovementioned range; conversely, a higher temperature promotes the synthesis of F125.

The contact time for the reaction according to the invention can be between 3 and 100 seconds, and more particularly between 5 and 30 seconds. However, in order to obtain a good compromise between the degree of conversion of the F123 and high productivities of F124 and/or F125, the best range is from 7 to 15 seconds.

The HF/pentahaloethane molar ratio can range from 1/1 to 20/1 and preferentially from 2/1 to 9/1. There again, the degree of conversion of the F123 and the distribution of the products formed vary with the molar ratio chosen, an increase in the molar ratio leading to an improvement in the degree of conversion of the F123 and to a shift of the products formed towards more fluorinated compounds (F125). However, it is necessary to note that a low molar ratio (less than 2) increases the formation of products which can not be recycled (perhaloethanes and tetrahaloethanes).

The fluorination reaction according to the invention can be carried out in a gas phase fluorination reactor in a stationary bed or in a fluid bed. The materials used for constructing the plant must be compatible with the presence of hydracids such as HCl and HF; they can be chosen from "Hastelloy" or from "Inconel" which are resistant to corrosive media containing these hydracids.

The fluorination reaction according to the invention can be carried out at atmospheric pressure or at a pressure greater than the latter. For practical reasons, the reaction will generally be carried out in a region ranging from 0 to 25 bar relative.

Under operating conditions which are capable of fouling the catalyst, it can be judicious to introduce a small content of oxygen with the reactants. This content can vary depending on the operating conditions between 0.02 and 5% with respect to the organic reactants (molar percentage). The object of this oxidizing agent is to react with the "heavies" which are the source of the fouling of the catalyst.

The use of the process according to the invention makes it possible to obtain the two desired pentahaloethanes F124 and F125 with an excellent selectivity (equal to or greater than approximately 90%), the proportion of a-isomers and of products which cannot be recycled (perhaloethanes and tetrahaloethanes) being very low. The process according to the invention also has great flexibility; from F123, the F124/F125 molar ratio in the product obtained can vary from 10/1 to 1/10 depending on the operating conditions. Moreover, the possibility of carrying out the reaction with low molar ratios and low contact times makes it possible to obtain a good productivity, while having a satisfactory degree of conversion of the F123.

The underfluorinated products optionally formed (F122: 0–0.2% and F1111: 0.1–1.2%) can be recycled with the unconverted F123 and F123a. If desired, the compounds F124 and F124a can also be recycled to the reactor to increase the productivity of F125.

EXAMPLES

The following example illustrates the invention without limiting it.

EXAMPLE

A—PREPARATION AND ACTIVATION OF THE CATALYST 250 ml of a support containing, by weight, 73% of aluminium fluoride and 27% of alumina, obtained in a preceding stage by fluorination of Grace HSA alumina in a fluidized bed at around 300° C. using air and hydrofluoric acid (concentration by volume of 5 to 10% of this acid in the air), were placed in a rotary evaporator. The starting Grace HSA alumina had the following physico-chemical characteristics:
shape: beads with a diameter of 1–2 mm
BET surface: 220 m$^2$/g
pore volume: 1.2 cm$^3$/g (for pore radii between 4 nm and 63 μm)
sodium content: 600 ppm.

Moreover, two separate aqueous solutions were prepared:
(a) chromium solution to which nickel chloride had been added, containing:
chromic anhydride: 25 g
nickel chloride hexahydrate: 58 g
water: 40 g
(b) methanol solution containing:
methanol: 35 g
water: 30 g The mixture of these two solutions was then introduced, at room temperature, under atmospheric pressure and over approximately 45 minutes, onto the support with stirring. The catalyst was then dried under a nitrogen stream, in a fluidized bed, at around 110° C. for 4 hours.

100 ml (77.5 g) of dry catalyst were charged to a tubular reactor made of Inconel with an internal diameter of 27 mm and the temperature was raised to 120° C. under a nitrogen stream at atmospheric pressure. This treatment was maintained for about ten hours and then the nitrogen was progressively replaced by hydrofluoric acid, care being taken that the increase in temperature did not exceed 95° C., and, when a HF/N$_2$ molar ratio of 50/50 was reached, the temperature was raised to 300° C.

After disappearance of the exotherm peaks, the temperature was raised to 350° C. under a stream of pure hydrofluoric acid (1 mol/hour) for 6 hours.

The catalyst was finally purged under a nitrogen stream before starting the catalytic test. The characteristics of the thus dried and activated catalyst were the following:
chemical composition (by weight)
  fluorine: 58.5%
  aluminium: 25.1%
  nickel: 6.8%
  chromium: 5.6%
  oxygen: 4%
physical properties:
  BET surface: 15.1 m$^2$/g
  volume of the pores with a radius between 4 nm and 63 μm: 0.382 cm$^3$/g
  surface of the pores with a radius greater than 4 nm: 18 m$^2$/g

B—FLUORINATION OF F123

The behaviour of the catalyst in the fluorination of F123 was tested at atmospheric pressure, without addition of oxygen, under the operating conditions and with the results collated in the following Table 1.

The F123 used was a crude product consisting essentially of F123 (96.1%), the other compounds being F123a (3.6%), F123b (less than 0.1%) and F113 (approximately 0.1%).

TABLE 1

| TEST No. | B1 | B2 |
| --- | --- | --- |
| Operating conditions: | | |
| Temperature (°C.) | 350 | 300 |
| HF/F123 molar ratio | 5.5 | 2.9 |
| Contact time (s) | 9.8 | 10.9 |
| Age of the catalyst (h) | 41 | 81 |
| Results: | | |
| Overall degree of conversion of F123 (%) | 81.6 | 44.2 |
| Selectivity (mol %) towards: | | |
| F125 | 56.7 | 10.7 |
| F124 | 42.2 | 87.1 |
| F124a | 0.1 | 0.2 |
| F123a | 0.1 | 0.2 |
| F133a | 0.3 | traces |
| F115 | 0.2 | 0 |
| F114 + F114a (C$_2$F$_4$Cl$_2$) | 0.3 | 0.1 |
| F1111 (CFCl=CCl$_2$) | 0.1 | traces |

C—FLUORINATION OF F124

The behaviour of the same catalyst in the fluorination of F124 was tested at atmospheric pressure, without addition of oxygen, under the operating conditions and with the results collated in the following Table 2. The starting F124 contained 0.9% of F124a isomer.

TABLE 2

| TEST No. | C1 | C2 |
| --- | --- | --- |
| Operating conditions: | | |
| Temperature (°C.) | 350 | 300 |
| HF/F124 molar ratio | 3 | 2.9 |
| Contact time (s) | 13.1 | 10.2 |
| Age of the catalyst (h) | 30 | 75 |
| Results: | | |
| Overall degree of conversion of F124 (%) | 86.7 | 89.7 |
| Selectivity (mol %) towards: | | |
| F125 | 91.1 | 89.8 |
| F124a | 0.2 | 0.3 |
| F123 | 7.4 | 5.4 |
| F123a | traces | traces |
| F133a | 0.5 | 1.3 |
| F115 | 0.3 | 1.3 |
| F114 + F114a ($C_2F_4Cl_2$) | 0.3 | 0.6 |
| F1111 (CFCl=$CCl_2$) | 0.1 | 0.3 |
| F1110 ($CCl_2$=$CCl_2$) | 0.1 | 0.3 |

We claim:

1. Process for the preparation of:
   (i) a mixture of 1,1,1,2-tetrafluoro-2-chloroethane (F124) and pentafluoroethane (F125), starting from a pentahaloethane selected from the group consisting of 1,1,1-trifluoro-2,2-dichloroethane (F123) and its mixture with 1,2-dichloro-1,1,2-trifluoroethane (F123a), or
   (ii) a pentafluoroethane (F125) starting from a pentahaloethane selected from the group consisting of 1,1,1,2-tetrafluoro-2-chloroethane (F124), 1-chloro-1,1,2,2-tetrafluoroethane (F124a), 1,1-dichloro-1,2,2-trifluoroethane (F123b) and mixtures thereof, comprising catalytically fluorinating said pentahaloethane in the gas phase with hydrofluoric acid and a mixed catalyst, said mixed catalyst comprising oxides, halides and/or oxyhalides of nickel and chromium deposited on a support of aluminum fluoride or of a mixture of aluminum fluoride and alumina, the content, by weight, of nickel and chromium in the catalyst being between 0.5 and 20% for each metal, the nickel/chromium atomic ratio being between 0.5 and 5, and recovering the mixture of F124 and F125 when practicing the above (i) or F125 when practicing the above (ii), each synthesized with substantial selectivity and productivity.

2. Process according to claim 1, wherein the content, by weight, of nickel and chromium in the catalyst is between 0.5 and 20% for each metal, the nickel/chromium atomic ratio being between 0.5 and 5.

3. Process according to claim 2, wherein the content is between 2 and 10% for each metal.

4. Process according to claim 1, wherein the hydrofluoric acid and the pentahaloethane(s) are brought into contact in a HF/pentahaloethane(s) molar ratio between 1/1 and 20/1, for a time between 3 and 100 seconds and at a temperature between 250° and 470° C.

5. Process according to claim 4, wherein the molar ratio is between 2/1 and 9/1, the contact time is between 5 and 30 seconds, and the temperature is between 280° and 410° C.

6. Process according to claim 1, wherein the process is carried out at a pressure ranging from 0 to 25 bar relative.

7. Process according to claim 1, wherein the reaction is carried out in the presence of oxygen.

8. Process according to claim 2, wherein the atomic ratio is about 1.

9. Process according to claim 5, wherein the contact time is between 7 and 11 seconds.

10. Process according to claim 6, wherein the pressure is atmospheric pressure.

11. Process for the preparation of:
    (i) a mixture of 1,1,1,2-tetrafluoro-2-chloroethane (F124) and pentafluoroethane (F125), starting from a pentahaloethane selected from the group consisting of 1,1,1-trifluoro-2,2-dichloroethane (F123) and its mixture with 1,2-dichloro-1,1,2-trifluoroethane (F123a), or
    (ii) a pentafluoroethane (F125) starting from a pentahaloethane selected from the group consisting of 1,1,1,2-tetrafluoro-2-chloroethane (F124), 1-chloro-1,1,2,2-tetrafluoroethane (F124a), 1,1-dichloro-1,2,2-trifluoroethane (F123b) and mixtures thereof, comprising catalytically fluorinating said pentahaloethane in the gas phase with hydrofluoric acid and a catalyst consisting of nickel and chromium compounds in the form of oxides, halides and/or oxyhalides deposited on a support of aluminum fluoride or of a mixture of aluminum fluoride and alumina; said nickel and chromium compounds being deposited on said support by impregnation; the content of nickel and chromium in the catalyst being between 0.5 and 20% by weight for each metal; and the nickel/chromium atomic ratio being between 0.5 and 5, and recovering the mixture of F124 and F125 when practicing the above (i) or F125 when practicing the above (ii), each synthesized with substantial selectivity and productivity.

12. The process of claim 11 wherein impregnation includes:
    (a) said support being combined with an aqueous solution of chromic acid ($CrO_3$) and a nickel salt, and said chromic acid being reduced; or
    (b) said support being combined with an aqueous solution of chromium and nickel salts.

13. The process of claim 11 wherein said chromic acid is reduced by inclusion of a reducing agent in the aqueous solution, or by thermal reduction.

14. The process of claim 1 wherein said nickel and chromium compounds are deposited on all of said support by impregnation.

15. The process of claim 1 wherein said pentahaloethane is selected from the group consisting of 1,1,1,2-tetrafluoro-2-chloroethane (F124), 1-chloro-1,1,2,2-tetrafluoroethane (F124a), 1,1-dichloro-1,2,2-trifluoroethane (F123b) and mixtures thereof; and wherein F125 is synthesized with substantial selectivity and productivity and recovered.

16. The process of claim 1 wherein the hydrofluoric acid/pentahaloethane molar ratio is between 2/1 to 9/1 to minimize the proportion of unrecyclable reaction products of a-isomers, perhaloethanes and tetrahaloethanes.

17. A process for the preparation of a mixture of 1,1,1,2-tetrafluoro-2-chloroethane and pentafluoroethane comprising the steps of:

catalytically fluorinating a pentahaloethane selected from the group consisting of 1,1,1-trifluoro-2,2-dichloroethane and its mixture with 1,2-dichloro-1,1,2-trifluoroethane in the gas phase with hydrofluoric acid and a mixed catalyst;

said mixed catalyst comprising oxides, halides and/or oxyhalides of nickel and chromium being deposited on a support of aluminum fluoride or of a mixture of aluminum fluoride and alumina; the content of nickel and chromium in the catalyst being between 0.5 and 20%, by weight, for each metal; and the nickel/chromium atomic ratio being between 0.5 and 5; and recovering 1,1,1,2-tetrafluoro-2-chloroethane and pentahaloethane, each synthesized with substantial selectivity and productivity.

18. The process of claim 17 wherein said mixed catalyst consists of said oxides, halides and/or oxyhalides of nickel and chromium deposited on said a support.

19. The process of claim 17 wherein said oxides, halides and/or oxyhalides of nickel and chromium are deposited by impregnation on said support.

20. The process of claim 17 wherein the hydrofluoric acid/pentahaloethane molar ratio is between 2/1 to 9/1 to minimize the proportion of unrecyclable reaction products of a-isomers, perhaloethanes and tetrahaloethanes; and further comprising recycling (a) unreacted F123 and 123a, (b) underfluorinated reaction products F122 and F1111, and (c) reaction products F124 and F124a to increase the productivity of F125.

21. The process of claim 17 wherein the selectivity for F124 and F125 is ≧90%; and wherein the hydrofluoric acid/pentahaloethane molar ratio is between 2/1 to 9/1 to minimize the proportion of unrecyclable reaction products of a-isomers, perhaloethanes and tetrahaloethanes.

22. The process of claim 17 wherein the hydrofluoric acid/pentahaloethane molar ratio is between 2/1 to 9/1, the reactant contact time is between 3 and 100 seconds, and the reaction temperature is between 280° and 410° C.

23. The process of claim 22 wherein the temperature is between 300° and 330° C. for directing the reaction to a preferential synthesis of F124, or between 330° and 410° C. for directing the reaction to a preferential synthesis of F125; and wherein the F124/F125 molar ratio in the reaction product is adjustable from 10/1 to 1/10.

* * * * *